United States Patent [19]

Sprague

[11] 4,228,180
[45] Oct. 14, 1980

[54] 7-OXABICYCLOHEPTANE AND 7-OXABICYCLOHEPTENE PROSTAGLANDIN ANALOGS

[75] Inventor: Peter W. Sprague, Pennington, N.J.

[73] Assignee: E. R. Squibb & Sons, Inc., Princeton, N.J.

[21] Appl. No.: 90,226

[22] Filed: Nov. 1, 1979

[51] Int. Cl.³ .................. A61K 31/34; A61K 31/557; C07D 307/28
[52] U.S. Cl. ............................... 424/285; 260/346.22
[58] Field of Search .................... 260/346.22; 424/285

[56] References Cited

U.S. PATENT DOCUMENTS

| | | | |
|---|---|---|---|
| 4,112,224 | 9/1978 | Bundy | 542/426 |
| 4,143,054 | 3/1979 | Sprague | 260/346.22 |

OTHER PUBLICATIONS

Wlodawer et al., J.A.C.S. 93, 2815–2816 (1971).
Bundy, Tet. Letters 24, 1957–1960 (1975).
Rose et al., Proc. Soc. Exp. Biol. & Med., 153, 209–212 (1976).
Corey et al., J.A.C.S. 98, 6417–6418 (1976).
Hamburg et al., Proc. Nat. Acad. Sci., U.S.A. 70, 899–903 (1973).
Gorman et al., Proc. Nat. Acad. Sci., U.S.A. 74, 4007–4011 (1977).
Eggette et al., J. Chem. Soc. Perkin I, pp. 980–989, (1978).

Primary Examiner—Henry R. Jiles
Assistant Examiner—Bernard Dentz
Attorney, Agent, or Firm—Lawrence S. Levinson; Burton Rodney

[57] ABSTRACT

New 7-oxabicycloheptane and 7-oxabicycloheptene prostaglandin analogs which have the general formula

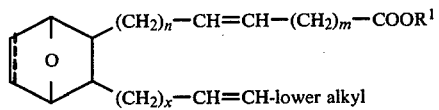

wherein $R^1$ is hydrogen or lower alkyl; n is 0 to 4, m is 0 to 4 and x is 0 to 8, are useful as cardiovascular agents.

11 Claims, No Drawings

7-OXABICYCLOHEPTANE AND 7-OXABICYCLOHEPTENE PROSTAGLANDIN ANALOGS

SUMMARY OF THE INVENTION

This invention relates to a group of compounds of the PGH$_2$ type and intermediates therefor which are cardiovascular agents useful, for example, in the treatment of thrombolytic disease. These compounds have the structural formula

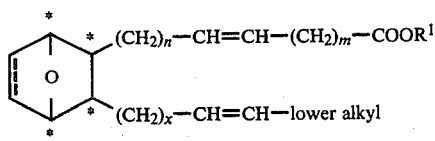

wherein R$^1$ is hydrogen or lower alkyl; n is 0 to 4, m is 0 to 4, and x is 0 to 8.

The term "lower alkyl" as employed herein includes both straight and branched chain radicals of up to 8 carbons, preferably 1 to 4 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl and the like as well as such groups including a halo-substituent, such as F, Br, Cl or I or CF$_3$ or a phenyl substituent.

The terms "(CH$_2$)$_n$, (CH$_2$)$_m$ and (CH$_2$)$_x$" each include a single bond or straight or branched chain radicals having from 1 to 4 carbons in the normal chain in the case of (CH$_2$)$_n$ and (CH$_2$)$_m$ and from 1 to 8 carbons in the normal chain in the case of (CH$_2$)$_x$ and may contain one or more lower alkyl substituents. Examples of (CH$_2$)$_n$, (CH$_2$)$_m$ or (CH$_2$)$_x$ groups include CH$_2$, CH$_2$CH$_2$, (CH$_2$)$_3$, (CH$_2$)$_4$, (CH$_2$)$_5$,

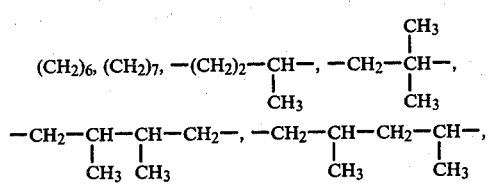

and the like.

DETAILED DESCRIPTION OF THE INVENTION

The sequence of reactions described below yields a series of 7-oxabicycloheptane- and 7-oxabicycloheptene-derivatives of the PGH$_2$ type.

Not only can members of the group be derived from other members and thus have utility as intermediates, but they also have physiological activity themselves.

Thus, when maleic anhydride is made to react with an unsubstituted or substituted furan having the formula

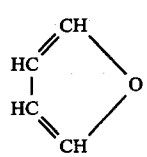

e.g., in ether solution at room temperature, this results in a compound having the formula

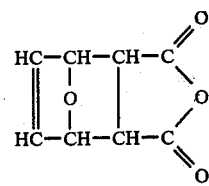

Reduction of the compound of formula III, e.g., catalyticaly, for example, in the presence of palladium-carbon, provides a reduced product having the formula

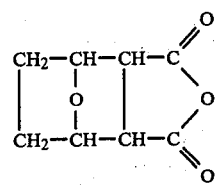

The compound of formula IV can then be converted to a compound having the formula

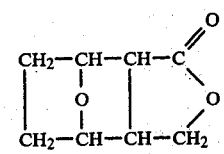

e.g., by reduction in tetrahydrofuran with a borohydride like sodium borohydride or zinc borohydride.

Treatment of the compound of formula V with diisobutylaluminum hydride or diisobutylborane yields a compound having the formula

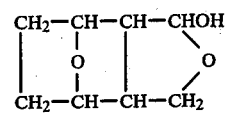

To form compounds of formula I wherein (CH$_2$)$_n$ is a single bond (and (CH$_2$)$_m$ is (CH$_2$)$_4$), the compound VI is subjected to Wittig reaction conditions, e.g., with a triphenyl phosphonium acid compound of the structure

to form a compound of the structure

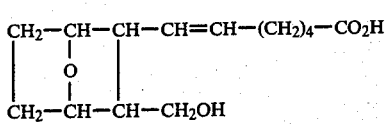

After esterification, the hydroxymethyl group in the compound of formula VIII is next oxidized, e.g., with chromium trioxide in pyridine, to obtain the aldehyde compound having the formula

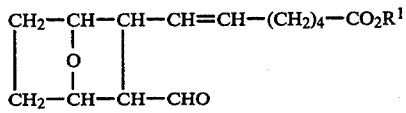   IX

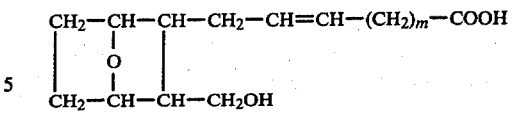   XIII

The side chain $(CH_2)_x$—CH=CH—lower alkyl is now ready to be added to compound IX in a manner as described hereinafter to form formula Ia compounds of the invention

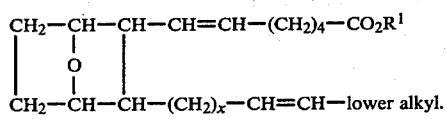   Ia

To form compounds of formula I wherein $(CH_2)_n$ is other than a single bond, for example where $(CH_2)_n$ is $CH_2$ and $(CH_2)_m$ is $(CH_2)_3$, the formula VI compound is submitted to Wittig reaction conditions, e.g., with an (alkoxymethyl)triphenylphosphonium halide like (methoxymethyl)triphenylphosphonium chloride in the presence of an alkali metal alkylamide like lithium diisopropylamide, a lithium alkyl like n-butyl lithium in an inert organic medium like toluene, tetrahydrofuran or the like, at a temperature in the range of about $-10°$ to $25°$ C.

This reaction produces a compound having the formula

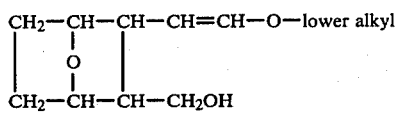   X

This product of formula X is acylated, e.g., with an acylpyridinium halide like N-acetylpyridinium chloride in the presence of an acid acceptor like pyridine, oxidized with an oxidizing agent like mercuric acetate in an organic medium like tetrahydrofuran, then demetalated with a reducing agent like potassium iodide to yield a product having the formula

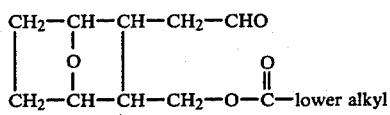   XI

Alternatively, the product of formula X is treated with an acid like formic acid or trifluoroacetic acid to yield a product having the formula

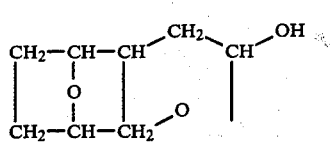   XII

These products of formulae XI or XII are subjected to a Wittig reaction, e.g., with a carboxyalkyl triphenylphosphonium halide to obtain a product having the formula By esterifying the product of formula XI, e.g., with a diazoalkane like diazomethane in an inert organic solvent like ether or with a substituted diazoalkane like diphenyldiazomethane, the lower alkyl ester or substituted lower alkyl ester of that compound (i.e., $R^1$ is lower alkyl) is obtained.

The hydroxymethyl group in the 3-position of this ester is next oxidized, e.g., with chromium trioxide in pyridine, to obtain the aldehyde compound having the formula

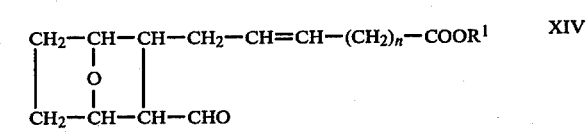   XIV wherein $R^1$ is lower alkyl.

The side chain $(CH_2)_x$—CH=CH—lower alkyl is now ready to be added in a manner as described hereinafter to form formula Ib compounds of the invention

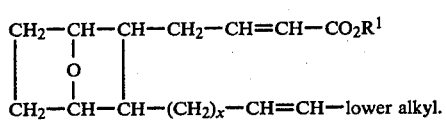   Ib

Where $(CH_2)_n$ is $(CH_2)_2$ in the formula I compounds of the invention and $(CH_2)_m$ is $(CH_2)_2$, the products of formulae XI or XII may be reacted with an alkoxy methyl triphenyl phosphonium halide $((C_6H_5)_3P=CHO\text{lower alkyl})$ under Wittig conditions to form a compound of the structure

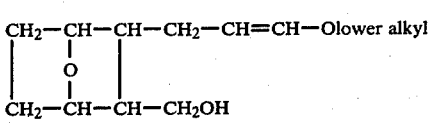   XIII which is then treated with an acid like formic acid, to yield the corresponding aldehyde of the structure

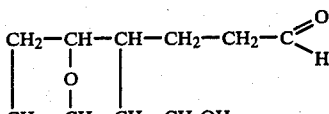   XIV

Compound XIV is next subjected to Wittig reaction conditions, and reacted with a triphenyl phosphonium acid $(C_6H_5)_3P=CH(CH_2)_2COOH$ to form a compound of the structure

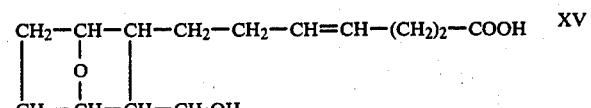   XV

After esterification and oxidation as described above with respect to the preparation of the aldehyde XIV, compound XVI is formed. The aldehyde group

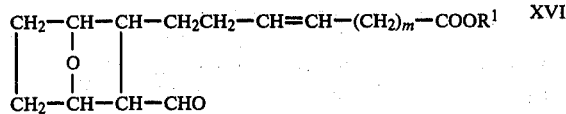

is then replaced with the $(CH_2)_x$—CH=CH-lower alkyl side chain as described hereinafter to form formula Ic compounds of the invention

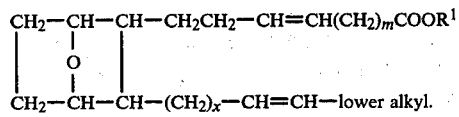

Where $(CH_2)_n$ is $(CH_2)_3$ in the formula I compounds of the invention and $(CH_2)_m$ is —$CH_2$—, the product of Formula XIV may be reacted with an alkoxy methyl triphenyl phosphonium halide $((C_6H_5)_3P=CHOlower$ alkyl) under Wittig conditions to form a compound of the structure

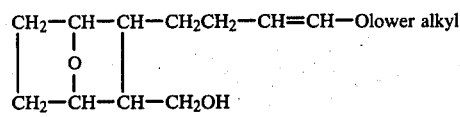

which is then treated with an acid like formic acid, to yield the corresponding aldehyde of the structure

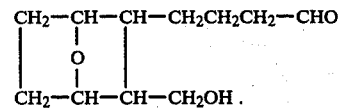

The compound XIVb may be reacted with a triphenyl phosphonium acid $(C_6H_5)_3P=CH(CH_2)COOH$ to form a compound of the structure

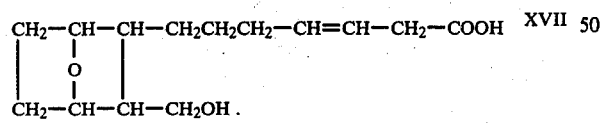

Again, as in the case of the preparation of compounds of formula Ic, after esterification and oxidation of XVIII to the corresponding aldehyde

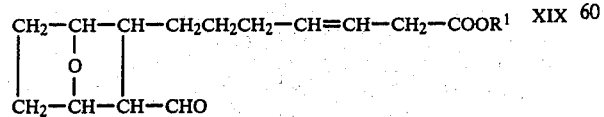

the aldehyde is replaced by the side chain $(CH_2)_x$—CH=CH—lower alkyl to form formula Id compounds of the invention

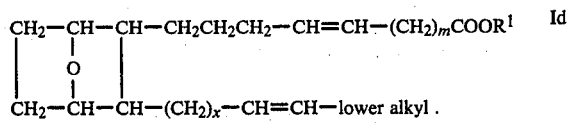

Where $(CH_2)_n$ is $(CH_2)_4$ in the formula I compounds of the invention and $(CH_2)_m$ is a single bond, the product of formula XIVb may be reacted with an alkoxy methyl triphenyl phosphonium halide $((C_6H_5)_3P=CHOlower$ alkyl) under Wittig conditions to form a compound of the structure

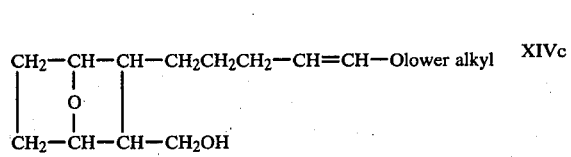

which is then treated with an acid like formic acid, to yield the corresponding aldehyde of structure

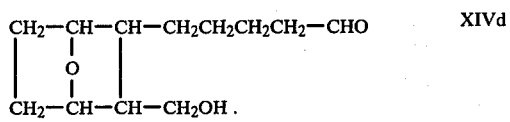

Compound XIVb may be reacted with a triphenyl phosphonium acid $((C_6H_5)_3P=CHCOOH)$ to form a compound of the structure

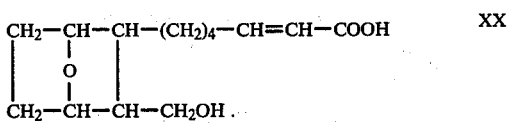

After esterification and oxidation to the aldehyde XXI

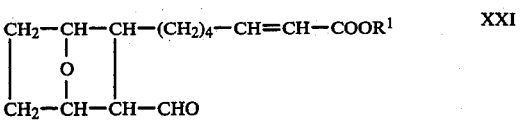

the aldehyde group is replaced by the side chain $(CH_2)_x$—CH=CH-lower alkyl to form formula Ie compounds of the invention

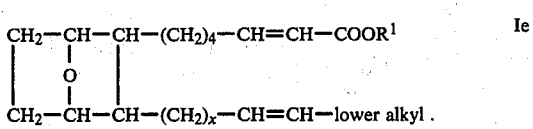

It will be appreciated that in the formulae Ia, Ib, Ic, Id and Ie compounds of the invention that the sum of n+m will always be 4. Furthermore, where $R^1$ is lower alkyl, the compounds of formulae Ia–Ie may be converted to the free acid by treatment with a base, such as lithium hydroxide followed by neutralization with an acid, such as dilute hydrochloric acid

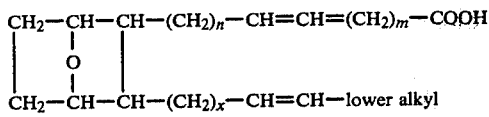

The side chain —(CH$_2$)$_x$—CH=CH—lower alkyl may be attached to the aldehyde

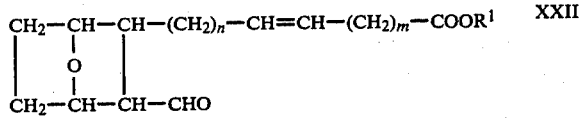

to form the formula I compounds of the invention. For example, where (CH$_2$)$_x$ is a single bond, such compounds may be formed by reacting compound XXII with a triphenyl phosphonium compound (C$_6$H$_5$)P=CH(CH$_2$)$_x$CH$_3$ under Wittig reaction conditions as described above to form a compound of the structure

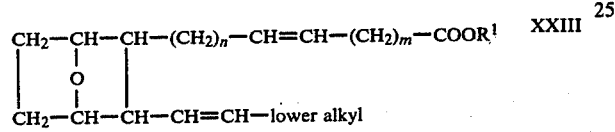

To form compounds of formula I wherein (CH$_2$)$_x$ is other than a single bond, for example, where (CH$_2$)$_x$ is —CH$_2$—, the formula XXII aldehyde is reacted with an alkoxy methyl triphenyl phosphonium halide ((C$_6$H$_5$)$_3$P=CHOlower alkyl) under Wittig conditions to form a compound of the structure

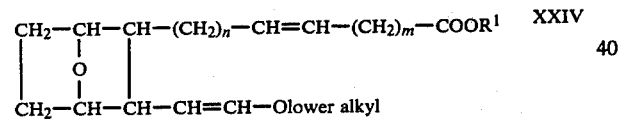

which is then treated with an acid like formic acid to yield the corresponding aldehyde

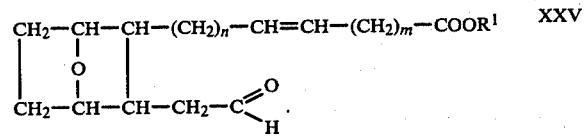

Aldehyde XXV is next subjected to Wittig reaction conditions, and reacted with a triphenyl phosphonium compound (C$_6$H$_5$)$_3$P=CH(CH$_2$)$_{x-1}$CH$_3$ to form formula If compounds of the invention

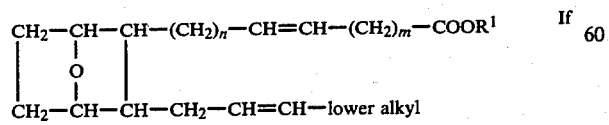

To form compounds of formula I wherein (CH$_2$)$_x$ is CH$_2$CH$_2$, the aldehyde XXV is reacted with the triphenyl phosphonium compound (C$_6$H$_5$)$_3$P=CHOlower alkyl to form

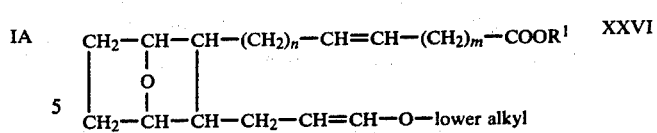

which is then hydrolyzed to the corresponding aldehyde

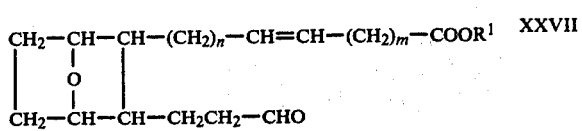

Aldehyde XXVII is then reacted with the triphenyl phosphonium compound (C$_6$H$_5$)$_3$P=CH(CH$_2$)$_{x-2}$CH$_3$ to form formula Ig compounds of the invention

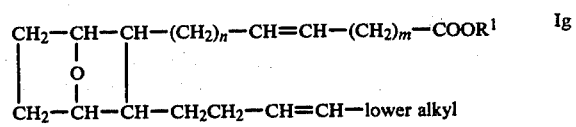

It will also be appreciated that the value of x in (CH$_2$)$_x$ in the compounds of formula I will depend on the number of moles of alkoxy methyl triphenyl phosphonium compound that is reacted with the appropriate aldehyde (containing (CH$_2$)$_y$) and the number of CH$_2$ units present in the triphenyl phosphonium compound (C$_6$H$_5$)$_3$P=CH(CH$_2$)$_q$CH$_3$ reacted with the appropriate aldehyde containing (CH$_2$)$_{y+1}$.

If, instead of reacting the unsubstituted or substituted furan of formula II with maleic anhydride, it is made to react with maleic acid, e.g., in water at room temperature, the unsaturated product having the formula

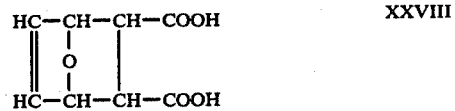

is obtained.

This can then be converted by reaction with an acid anhydride such as trifluoroacetic acid anhydride followed by treatment with a reducing agent such as sodium borohydride to the 5,6-unsaturated analog of a compound of formula V above, i.e., a compound having the formula

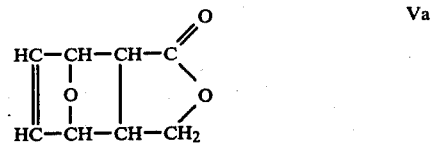

Starting with this compound instead of with the compound of formula V and following the same sequence of steps as described above with respect to the latter compound and its successor compounds, there are obtained compounds corresponding to those of formulas VI to XXVII inclusive but having a double bond in the 5,6-position.

Additionally, the compound of formula Va can be reduced, e.g., with hydrogen over palladium on carbon to obtain a compound of formula V and this intermediate processed as described above.

The symbols in the foregoing formulae and throughout this specification have the meanings defined above. The lower alkyl and lower alkylene groups are straight or branched chain aliphatic hydrocarbon radicals having up to seven carbon atoms, e.g., methyl, ethyl, propyl, isopropyl, butyl, t-butyl, amyl and the like. The $C_1$-$C_4$ and especially the $C_3$-$C_4$ members are preferred.

Preferred compounds are compounds of formula I, wherein $R^1$ is hydrogen or lower alkyl, particularly $C_1$-$C_4$ lower alkyl and especially methyl, n is 1, m is 3, x is 0, and the lower alkyl group has 3 or 4 carbons in a linear chain. Compounds without the optional double bond are preferred over those with the double bond. The products of the examples constitute preferred embodiments as well as provide additional experimental details and serve as models for additional members of the group.

The compounds of this invention have centers of asymmetry as indicated by the asterisks in formula I. The various stereoisomeric forms are within the scope of the invention.

Thus, when the first sequence of reactions described above are followed, i.e., reacting maleic anhydride with a furan of formula II, compounds are obtained wherein both side chains, i.e., those residues attached to the 2- and 3-positions on the 7-oxabicyclo[2,2,1]heptane ring system, are cis to the 7-oxa bridge.

These can be shown by the common method of depicting steric structure as follows with respect to a compound of formula VI, for example

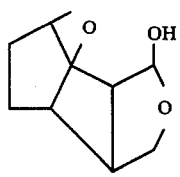

XXIX the right hand ring being in the exo position. All stereoisomeric pairs can be resolved by conventional techniques, such as chromatography on silica gel.

On the other hand, when the alternate procedures described above are used, e.g., reacting a furan with maleic acid and optionally reducing the double bond, stereo-isomeric compounds are obtained wherein the lactole ring and subsequent compounds are in the endo position as depicted graphically with respect to a compound of formula XXIX:

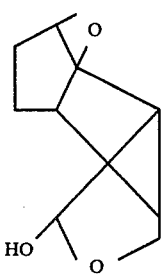

XXIXa

Various stereoisomers of compounds of formula I of the invention may be obtained employing related starting materials as described in U.S. Pat. No. 4,143,054 employing reaction conditions as described above; examples of such stereoisomers, are set out below.

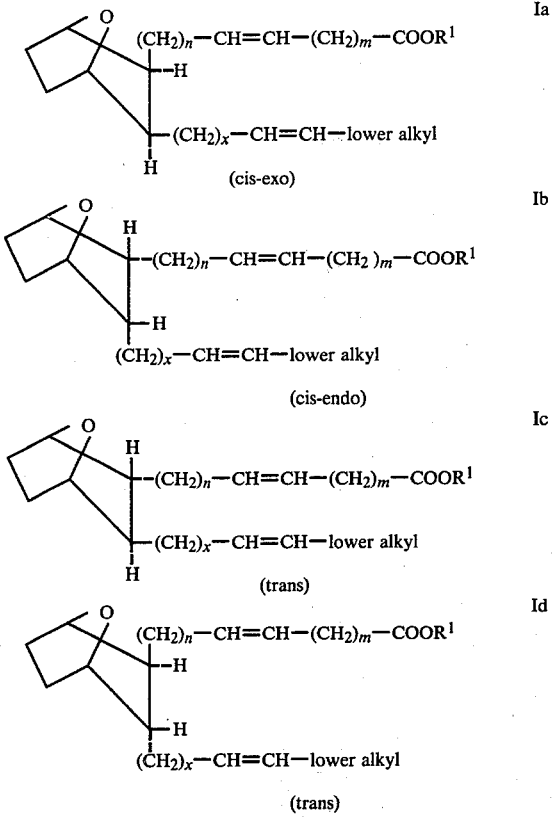

Additional experimental details are found in the examples which represent preferred embodiments.

The compounds of this invention are cardiovascular agents useful as platelet aggregation inhibitors, e.g., for treatment of thrombolytic disease, such as coronary or cerebral thromboses. They are also selective thromboxane $A_2$ synthetase inhibitors, e.g., having a vasodilatory effect for treatment of myocardial ischemic disease, such as angina pectoris. They can be administered orally or parenterally to various mammalian species known to be subject to such maladies, e.g., cats, dogs, and the like in an effective amount within the dosage range of about 1 to 100 mg/kg, preferably about 1 to 50 mg/kg and especially about 2 to 25 mg/kg on a regimen in single or 2 to 4 divided dialy doses.

The active substance can be utilized in a composition, such as tablet, capsule, solution or suspension containing about 5 to about 500 mg per unit of dosage of a compound or mixture of compounds of formula I. They may be compounded in conventional manner with a physiologically acceptable vehicle or carrier, excipient, binder, preservative, stabilizer, flavor, etc. as called for by accepted pharmaceutical practice. Also so indicated in the discussion above, certain members additionally serve as intermediates for other members of the group.

The following examples are illustrative of the invention. All temperatures are in degrees Celsius.

EXAMPLE 1

A. (Exo)Hexahydro-4,7-epoxyisobenzofuran-1,3-dione

A mixture containing 30.0 g (0.18 mole) of 7-oxabicyclo[2.2.1]-5-heptene-2,3-dicarboxylic anhydride [Ber.

62, 554 (1929); Ann. 460, 98(1928)], 1.5 g of 5% Pd/C and 1.5 l. of ethyl acetate is hydrogenated in an atmospheric hydrogenator. The reaction is stopped after uptake of 4.518 l. of hydrogen. The catalyst is filtered from the reaction mixture and the solvent is stripped off under vacuum to yield 29.8 g of (exo)hexahydro-4,7-epoxyisobenzofuran-1,3-dione, m.p. 112°–114°.

B. (Exo)Hexahydro-4,7-epoxyisobenzofuran-1(3H)-one

To a slurry of 6.7 g (0.18 mole) of sodium borohydride in 50 ml of dry tetrahydrofuran is added a solution of 29.8 g (0.18 mole) of (exo)hexahydro-4,7-epoxyisobenzofuran-1,3-dione in 500 ml of dry tetrahydrofuran over a 10 minute period with stirring and ice-bath cooling. The resulting mixture is stirred under nitrogen for 5 hours and then stripped of solvent under vacuum. The residue is treated with 100 ml of 10% hydrochloric acid solution while being cooled in an ice-bath. The resulting slurry is extracted with dichloromethane (5×100 ml) dried over sodium sulfate and concentrated to yield crystalline crude material. This is recrystallized from benzene-hexane to yield 20.1 g of (exo)-hexahydro-4,7-epoxyisobenzofuran-1(3H)-one, m.p. 112–118.

C. (Exo)Octahydro-4,7-epoxyisobenzofuran-1-ol

A solution of (exo)hexahydro-4,7-epoxyisobenzofuran-1(3H)-one (3 g, 0.02 moles) in 100 ml of anhydrous toluene is chilled to −78° and treated dropwise over ten minutes with a solution of diisobutyl aluminum hydride in toluene (1.5 molar, 26 ml, 0.04 moles). The resulting slurry is stirred at −78° for twenty minutes (a solution results). The reaction is quenched by adding a dropwise 24 ml of 10% acetic acid and allowing the reaction mixture to warm to room temperature. The mixture is then poured into 100 ml of 10% hydrochloric acid saturated with sodium chloride. The product is exhaustively extracted with dichloromethane (8×100 ml). The combined dichloromethane extracts are washed with 50 ml of 5% sodium bicarbonate, dried over sodium sulfate, and concentrated in vacuo. The resultant crystalline product is recrystallized from benzene to yield 2.4 g of (exo)octahydro-4,7-epoxyisobenzofuran-1-ol, m.p, 125°–127°.

D. (Exo)-3-(2-Methoxyethenyl)-7-oxabicyclo-[2.2.1]heptane-2-methanol

A slurry of (methoxymethyl)-triphenylphosphonium chloride (123.47 g, 0.36 moles) in anhydrous toluene (1700 ml) is chilled in an ice bath and treated dropwise over ten minutes with a solution of lithium diisopropylamide (38.6 g, 0.36 moles) in anhydrous tetrahydrofuran. The resulting red solution is stirred at 0° for ten minutes then treated via a solid addition device with (exo)octahydro-4,7-epoxyisobenzofuran-1-ol (18.7 g, 0.12 moles). The mixture is then stirred at room temperature for two hours. The mixture is poured into brine (1000 ml) and treated with 10% hydrochloric acid to pH 6.8. The mixture is extracted several times with diethyl ether. The combined ether extracts are dried over sodium sulfate and concentrated in vacuo. The residue is dissolved in diethyl ether (500 ml) and chilled overnight. The solid precipitate is filtered off and the filtrate concentrated in vacuo. The residue is chromatographed on silica gel (1500 ml) eluting with (1) dichloromethane and (2) ethyl acetate. The crude product contained in the ethyl acetate fractions is distilled in vacuo to yield 14.5 g of (exo)-3-(2-methoxyethenyl)-7-oxobicyclo-[2.2.1]heptane-2-methanol, b.p. 100°–105°/0.001 mm.

E. [1R-(1α,2β(4Z),3β,4α)]-7-[3-(Hydroxymethyl)-7-oxabicyclo-[2.2.1]hept-2-yl]-5-heptenoic acid (a) A mixture of N-acetylpyridinium chloride is prepared by adding 9.6 ml (135 mmole) of acetyl chloride dropwise to 56 ml of pyridine. To this is added 5.0 g (27 mmole) of (exo)-3-(2-methoxyethenyl)-7-oxobicyclo[2.2.1]-heptane-2-methanol dissolved in 5 ml of pyridine. The resulting mixture is stirred at room temperature for 1.5 hours and poured into brine. The product is extracted into ether (3×200 ml), the ether extracts are washed with 5% hydrochloric acid (2×400 ml) and brine (1×200 ml) and dried over sodium sulfate. Concentration yields a yellow oil which is purified by passage through a short column of silica gel (150 ml) with dichloromethane, yield 4.42 g of an oil.

(b) To a solution of 4.42 g (19.6 mmole) of the oil in 500 ml of tetrahydrofuran containing 50 ml of water is added 31.1 g (97.8 mmole) of mercuric acetate. The yellow suspension which forms is stirred for 10 minutes and then the entire mixture is poured into a solution containing 200 g of potassium iodide in 2 l. of water. Upon shaking, the yellow color disappears and the mixture is extracted with benzene (3×500 ml). The combined benzene extracts are washed with potassium iodide solution and brine and dried over sodium sulfate. Concentration yields 3.7 g of material which crystallizes on standing in an ice box.

(c) A Wittig reagent is prepared in dimethyl sulfoxide (dried over calcium hydride) by adding a solution of sodium methylsulfinylmethide (prepared by heating 300 mg of sodium hydride in 60 ml of dimethyl sulfoxide at 75° until hydrogen evolution stops) dropwise to a solution of 5.32 g (12 mmole) of 4-carboxybutyl triphenylphosphonium bromide in 100 ml of dimethyl sulfoxide. After the first orange color, lasting more than 10 seconds forms, an equivalent amount of base is added to form the ylide. To this deep orange solution is added a solution of the product of part (b) in 20 ml of dimethyl sulfoxide and the resulting mixture stirred at room temperature for 45 minutes. The reaction is quenched by addition of 24 mmole of acetic acid and the mixture poured into brine (300 ml) and extracted with ether (3×200 ml). Concentration of these extracts gives an oil which is stirred with saturated sodium bicarbonate solution until crystalline triphenylphosphine oxide forms in the mixture. This mixture is washed with benzene and acidified with 10% hydrochloric acid. The aqueous layer is saturated with salt and extracted with ether which on drying (sodium sulfate) and concentration gives 2.43 g of crude product. The mixture is stirred 24 hours with 10% aqueous sodium hydroxide and reisolated by acidification and ether extraction. The product is purified on 500 g of silica gel with 50/50 ethyl acetate-hexane as the eluant which gives 600 mg of acid which crystallizes on standing. This is recrystallized twice from ethyl acetate-cyclohexane to yield 320 mg of [1R-(1α,2β(Z),3β,4α)]-7-[3-(hydroxymethyl)-7-oxobicyclo[2.2.1]hept-2-yl]-5-heptenoic acid, m.p. 59°–63°.

F. [1R-(1α,2β(5Z),3β,4α)]-7-[3-(hydroxymethyl)-7-oxobicyclo[2.2.1]hept-2-yl]-5-heptenoic acid, methyl ester A solution of diazomethane in ether is prepared from 3 g of N-methylnitro-nitrosoguanidine in 50 ml of ether with dropwise addition at 0° of 9 ml of 40% potassium hydroxide/water solution. This solution (dried over potassium hydroxide pellets) is added dropwise to a stirring solution of [1R-(1α,2β(Z),3β,4α)]-7-[3-(hydroxymethyl)-7-oxabicyclo[2.2.1]hept-1-yl]-5-heptenoic acid (254 g, 10 mmole in ether (150 ml) over a ten minute period. Stirring is continued for one hour. The excess diazomethane is destroyed by the addition of acetic acid (1.5 ml). The solution is washed with 5% sodium bicarbonate solution, brine, dried over sodium sulfate, and concentrated in vacuo to yield 2.6 g of product (one spot by TLC—silica gel; ethyl acetate; ($R_f$=0.5). The residue is chromatographed on silica gel (200 ml) eluting with (1) ethyl acetate/pentane (1:9), (2) ethyl acetate/pentane (1:4), and (3) ethyl acetate/pentane (2:3) to yield 2.23 g of [1R-(1α,2β(5Z),3β,4α)]-7-[3-(hydroxymethyl)-7-oxabicyclo[2.2.1]hept-2-yl]-5-heptenoic acid, methyl ester as an oil.

G. [1R-(1α,2β(5Z),3β,4α)]-7-[3-formyl-7-oxabicyclo[2.2.1]hept-2-yl]-5-heptenoic acid, methyl ester A solution of chromium trioxide/pyridine is prepared in anhydrous dichloromethane (from 5.38 g, 54 mmole of chromium trioxide, 8.7 ml, 108 mmoles of pyridine and 200 ml of dichloromethane) and stirred at room temperature for twenty minutes. Eight grams of dry Celite (diatomaceous earth dried at 100° overnight) are then added followed by a solution of [1R-(1α,2β(5Z),3β,4α)]-7-[3-(hydroxymethyl)-7-oxabicyclo[2.2.1]hept-2-yl]-5-heptenoic acid, methyl ester (2.38 g, 8.94 mmoles in 15 ml of dichloromethane). The resulting mixture is stirred under nitrogen for fifteen minutes and then filtered. The filtrate is washed with 5% sodium bicarbonate solution (2×100 ml), 10% hydrochloric acid (2×100 ml), 5% sodium bicarbonate solution (2×100 ml), water (1×200 ml) and brine (2×100 ml). After drying over sodium sulfate, the dichloromethane solution is concentrated in vacuo to yield 2.6 g of crude product. The crude product is purified by column chromatography on Silicar CC-7 silica gel (300 ml) eluting with 10% ethyl acetate/hexane to yield 2.1 g of [1R-(1α,2β(5Z),3β,4α)]-7-[3-formyl-7-oxabicyclo[2.2.1-]hept-2-yl]-5-heptenoic acid, methyl ester as an oil.

EXAMPLE 2

A. [1R-(1α,2β(5Z),3β(1E),4α)]-7-[3-(1-Octenyl)-7-oxabicyclo[2.2.1]hept-2-yl]-5-heptenoic acid, methyl ester A slurry of triphenylheptylphosphonium bromide (17.64 g, 40 mmoles) in toluene (250 ml) is treated at room temperature with a solution of lithium diisopropylamide (prepared from 1.6 M n-butyl lithium (25 ml, 40 mmoles) and diisopropylamine (6.4 ml, 45 mmoles) in tetrahydrofuran (10 ml). The mixutre is stirred at room temperature for thirty minutes then treated with a solution of [1R-(1α,2β(5Z),3β,4α)]-7-[3-formyl-7-oxabicyclo[2.2.1]hept-2-yl]-5-heptenoic acid, methyl ester (5.32 g, 20 mmoles) in toluene (10 ml). The reaction mixture is stirred at room temperature for one hour then quenched with glacial acetic acid (2.4 g, 40 mmoles). The mixture is poured into brine and extracted with diethylether (3×100 ml). The combined ether extracts are washed with water (1×100 ml) and brine (1×100 ml), dried over magnesium sulfate and concentrated in vacuo. The residue is triturated with hexane. The precipitated phosphine salts are removed by filtration. The filtrate is concentrated in vacuo. The residue is chromatographed on 10–20μ silica gel (600 ml) eluting with hexane/dichloromethane (1:4) to yield 1.1 g of pure cis product, 530 mg of pure trans product, and 2.4 g of mixed fractions which contained approximately 5% trans product and 95% cis product.

B. [1R-(1α,2β(5Z),3β(1Z),4α)]-7-[3-(1-(Octenyl)l-7-oxabicyclo[2.2.1]hept-2-yl]-5-heptenoic acid, methyl ester This compound is isolated from the reaction mixture in A. above.

EXAMPLE 3

[1R-(1α,2β(5Z),3β(1Z),4α)]-7-[3-(1-Octenyl)-7-oxabicyclo[2.2.1]hept-2-yl]-5-heptenoic acid A solution of [1R-(1α,2β(5Z),3β(1E),4α)]-7-[3-(1-octenyl-7-oxabicyclo[2.2.1]hept-2-yl]-5-heptenoic acid, methyl ester (1.1 g, 3.2 mmoles) and lithium hydroxide monohydrate (1.65 g, 39 mmoles) in tetrahydrofuran/water (165 ml/55 ml) is stirred at room temperature for eight hours. The reaction mixture is concentrated in vacuo to approximately 60 ml. The mixture is then acidified with 10% oxalic acid to pH=2 and extracted with ether (3×50 ml). The combined ether extracts are dried over magnesium sulfate and concentrated in vacuo. The residue is chromatographed on 10–20μ silica gel (500 ml) eluting with dichloromethane and 30% ether/dichloromethane to yield 950 mg of desired product.

EXAMPLE 3A

[1R-(1α,2β(5Z),3β(1E),4α)]-7-[3-(1-Octenyl)-7-oxabicyclo[2.2.1]hept-2-yl]-5-heptenoic acid A solution of [1R-(1α,2β(5Z),3β(1Z),4α)]-7-[3-(1-octenyl)-7-oxabicyclo[2.2.1]hept-2-yl]-5-heptenoic acid methyl ester (530 mg, 1.5 mmoles) and lithium hydroxide monohydrate (795 mg, 19 mmoles) in tetrahydrofuran/water (80 ml/25 ml) is stirred at room temperature for 8 hours. The reaction mixture is concentrated in vacuo to approximately 30 ml. The mixture is then acidified to pH=2 with 10% oxalic acid and extracted with ether (3×50 ml). The combined ether extracts are dried over magnesium sulfate and concentrated in vacuo. The residue is chromatographed on 10–20μ silica gel (300 ml) eluting with dichloromethane and 30% ether/dichloromethane to yield 480 mg of desired product.

EXAMPLE 4

[1R-(1α,2β(4Z),3β-(1E),4α)]-7-[3-(1-Octenyl)-7-oxabicyclo[2.2.1]hept-2-yl]-4-heptenoic acid A. (Exo)octahydro-5,8-epoxy-1H-benzopyran-3-ol A solution of (exo)-3-(2-methoxyethenyl)-7-oxabicyclo[2.2.1]heptane-2-methanol prepared as described in Example 1, part D, (10.2 g, 0.055 mole) in 88% formic acid (166 ml) is prepared at 0° C. and stirred under nitrogen without cooling for 30 minutes. The reaction mixture is chilled in an ice bath and treated dropwise over 45 minutes with 10% sodium hydroxide solution until a pH of 7.5 is reached. The solution is saturated with sodium chloride and extracted several times with dichloromethane. The combined extracts are dried over sodium sulfate and concentrated to yield 8 g of product which is recrystallized from cyclohexane to yield 5.9 g of the title A compound, m.p. 101°–103° C.

B. (Exo)-3-(3-methoxy-2-propen1-yl)-7-oxabicyclo[2.2.1]heptane-b 2-methanol

Employing the procedure outlined in Example 1, part D, except substituting (exo)octahydro-5,8-epoxy-1H-benzopyran-3-ol for (exo)octahydro-4,7-epoxyisobenzofuran-1-ol, the title B compound is obtained.

C. [1R-(1α,2β,3β,4α)]-3-[3-(Hydroxymethyl)-7-oxabicyclo[2.2.1]hept-2-yl]propanal Employing the procedure outlined in Example 4, part A, except substituting the above title B compound for (exo)-3-(2-methoxyethenyl)-7-oxabicyclo[2.2.1]-heptane-2-methanol, the above title C compound is obtained.

D. [1R-(1α,2β(4Z),3β,4α)]-7-[3-(Hydroxymethyl)-7-oxabicyclo[2.2.1]hept-2-yl]-4-heptenoic acid Following the procedure outlined in Example 1, part E(c), except substituting [1R-(1α,2β,3β,4α)]-3-[3-(hydroxymethyl)-7-oxabicyclo[2.2.1]-hept-2-yl]-propanal for the 3-[3-(acetoxymethyl)-7-oxabicyclo[2.2.1]hept-2-yl]-ethanal, the Wittig reagent prepared from 3-carboxypropyl triphenylphosphonium bromide is used to form the title D compound.

E. [1R-(1α,2β(4Z),3β,4α)]-7-[3-(hydroxymethyl)-7-oxabicyclo[2.2.1]hept-2-yl]-4-heptenoic acid, methyl ester Following the procedure outlined in Example 1, part F, except substituting [1R-(1α,2β(4Z),3β,4α)]-7-[3-(Hydroxymethyl)-7-oxabicyclo[2.2.1]hept-2-yl]-4-heptenoic acid for [1R-(1α,2β(5Z),3β,4α)]-7-[3-(Hydroxymethyl)-7-oxabicyclo[2.2.1]hept-1-yl]-5-heptenoic acid, the title E compound is obtained.

F. [1R-(1α,2β(4Z),3β,4α)]-7-[3-Formyl-7-oxabicyclo[2.2.1]hept-2-yl]-4-heptenoic acid, methyl ester Following the procedure outlined in Example 1, part G, except substituting the above title E compound for the Example 1 part F compound, the title F compound is obtained.

G. [1R-(1α,2β(4Z),3β(1E),4α)]-2-[3-(1-Octenyl)-7-oxabicyclo[2.2.1]hept-2-yl]-4-heptenoic acid, methyl ester Following the procedure outlined in Example 2, part A except substituting the above title F compound for the Example 1 starting material, a mixture of the title G and title H compounds (mentioned below) is obtained.

H. [1R-(1α,2β(4Z),3β(1Z),4α)]-7-[3-(1-Octenyl)-7-oxabicyclo[2.2.1]hept-2-yl]-4-heptenoic acid, methyl ester This compound is isolated from the reaction mixture in part G above as described in Example 2 part B.

I. [1R-(1α,2β(4Z),3β(1Z),4α)]-7-[3-(1-Octenyl)-7-oxabicyclo[2.2.1]hept-2-yl]-4-heptenoic acid Following the procedure outlined in Example 3, except substituting the above title H compound for the Example 2 compound, the above title I compound is obtained.

J. [1R-(1α,2β(4Z),3β(1E),4α]-7-[3-(1-Octenyl)-7-oxabicyclo[2.2.1]hept-2-yl]-4-heptenoic acid Following the procedure outlined in Example 3, except substituting the above title G compound for the Example 2 compound, the above title J compound is obtained.

EXAMPLE 5

[1R-(1α,2β(3Z),3β(1Z),4α]-7-[3-(1-Octenyl-7-oxabicyclo[2.2.1]hept-2-yl]-3-heptenoic acid A. (Exo)-3-(4-methoxy-3-buten-1-yl)-7-oxabicyclo[2.2.1]heptane-2-methanol Following the procedure outlined in Example 1, part D, except substituting the Example 4 part C compound for the Example 1 part C compound, the title A compound is obtained.

B. [1R-(1α,2β,3β,4α)]-4-[3-(Hydroxymethyl)-7-oxabicyclo[2.2.1]hept-2-yl)]-butanal Following the procedure outlined in Example 4 part A, except substituting the Example 5 part A compound for the Example 1 part D compound, the above title B compound is obtained.

C. [1R-(1α,2β(3Z),3β,4α)]-7-[3-(Hydroxymethyl)-7-oxabicyclo[2.2.1]hept-2-yl]-3-heptenoic acid Following the procedure outlined in Example 1 part E(c), except substituting the above title B compound for the Example 1 part D compound, the Wittig reagent prepared from 2-carboxyethyltriphenyl phosphonium bromide is used to form the above Title C compound.

D. [1R-(1α,2β(3Z),3β,4α)]-7-[3-(Hydroxymethyl)-7-oxabicyclo[2.2.1]hept-2-yl]-3-heptenoic acid, methyl ester Following the procedure outlined in Example 1 part F, except substituting the above title C compound for the Example 1 part E compound, the above title D compound is obtained.

E. [1R-(1α,2β(3Z),3β,4α)]-7-[3-Formyl-7-oxabicyclo[2.2.1]hept-2-yl]-3-heptenoic acid, methyl ester Following the procedure outlined in Example 1 part G except substituting the above title D compound for the Example 1 part F compound, the above title E compound is obtained.

F. [1R-(1α,2β(3Z),3β(1E),4α)]-7-[3-(1-Octenyl)-7-oxabicyclo[2.2.1]hept-2-yl]-3-heptenoic acid, methyl ester Following the procedure outlined in Example 2 part A, except substituting the above title E compound for the Example 1 compound, the above title F compound is obtained in admixture with the title G compound set out below.

G. [1R-(1α,2β(3Z),3β(1Z),4α)]-7-[3-(1-Octenyl)-7-oxabicyclo[2.2.1]hept-2-yl]-3-heptenoic acid, methyl ester The title G compound is separated from its admixture with the title F compound as described in Example 2 part B.

H. [1R-(1α,2β(3Z),3β(1E),4α)]-7-[3-(1-Octenyl-7-oxabicyclo[2.2.1]hept-2-yl]-3-heptenoic acid Following the procedure outlined in Example 3, except substituting the above title F compound for the Example 2 compound, the above title H compound is obtained.

I. [1R-(1α,2β(3Z),3β(1Z),4α)]-7-[3-(1-Octenyl-7-oxabicyclo[2.2.1]hept-2-yl]-3-heptenoic acid Following the procedure outlined in Example 3, except substituting the above title G compound for the Example 2 compound, the above title I compound is obtained.

EXAMPLE 6

[1R-(1α,2β(2E),3β(1Z),4α)]-7-[3-(1-Octenyl)-7-oxabicyclo[2.2.1]hept-2-yl]-2-heptenoic acid A. (Exo)-5-(5-methoxy-4-penten-1-yl)-7-oxabicyclo[2.2.1]heptane-2-methanol Following the procedure outlined in Example 1 part D, except substituting the Example 5 part B compound for the Example 1 part C compound, the above title A compound is obtained.

B. [1R-(1α,2β,3β,4α)-5-[3-(Hydroxymethyl)-7-oxabicyclo[2.2.1]hept-2-yl]-pentanal Following the procedure outlined in Example 4 part A, except substituting the above title A compound for the Example 1 part D compound, the title B compound is obtained.

C. [1R-(1α,2β(2E),3β,4α)]-7-[3-(Hydroxymethyl)-7-oxabicyclo[2.2.1]hept-2-yl]-2-heptenoic acid, methyl ester A mixture of the above title B compound (2.12 g, 0.01 mole) and the stabilized Wittig reagent prepared from carbomethoxymethyl triphenyl phosphonium chloride (6.12 g, 0.02 mole) is prepared in chloroform and heated at reflux for 16 hours. The solvent is removed under vacuum and the residue purified by column chromatography on silica gel yielding 2.0 g of the above title C compound.

D. [1R-(1α,2β(2E),3β,4α)]-7-[3-Formyl-7-oxabicyclo[2.2.1]hept-2-yl]-2-heptenoic acid, methyl ester Following the procedure set out in Example 1, part G, except substituting the title C compound for the Example 1 part F compound, the title D compound is obtained.

E. [1R-(1α,2β(2E),3β(1E),4α)]-7-[3-(1-Octenyl)-7-oxabicyclo[2.2.1]hept-2-yl]-2-heptenoic acid, methyl ester Following the procedure of Example 2 part A, except substituting the above title D compound for the Example 1 compound, the title E compound is obtained in admixture with the title F compound named below.

F. [1R-(1α,2β(2E),3β(1Z),4α)]-7-[3-(1-Octenyl)-7-oxabicyclo[2.2.1]hept-2-yl]-2-heptenoic acid, methyl ester The title F compound is isolated from the title E compound as described in Example 2 part B.

G. [1R-(1α,2β(2E),3β(1E),4α)]-7-[3-(1-Octenyl)-7-oxabicyclo[2.2.1]hept-2-yl]-2-heptenoic acid Following the procedure outlined in Example 3 except substituting the above title E compound for the Example 2 part A compound, the above title G compound is obtained.

H. [1R-(1α,2β(2E),3β(1Z),4α)]-7-[3-(1-Octenyl)-7-oxabicyclo[2.2.1]hept-2-yl]-2-heptenoic acid Following the procedure outlined in Example 3 except substituting the above title F compound for the Example 2 part A compound, the above title H compound is obtained.

EXAMPLE 7

[1R-(1α,2β-(6Z),3β(1Z),4α)]-7-[3-(1-Octenyl)-7-oxabicyclo[2.2.1]hept-2yl]-6-heptenoic acid A. [1R-(1α,2β(6Z),3β,4α)]-7-[3-(Hydroxymethyl)-7-oxabicyclo[2.2.1]hept-2-yl]-6-heptenoic acid Following the procedure outlined in Example 1 part E(c), the Wittig reagent prepared from 6-carboxypentyl triphenyl phosphonium bromide is used to convert the Example 1 part C compound to the above title A compound.

B. [1R-(1α,2β(6Z),3β,4α)]-7-[3-(Hydroxymethyl)-7-oxabicyclo[2.2.1]hept-2-yl]-6-heptenoic acid, methyl ester Following the procedure outlined in Example 1 part F, the above title A compound is converted to the title B compound.

C. [1R-(1α,2β(6Z),3β,4α)]-7-[3-Formyl-7-oxabicyclo[2.2.1]hept-2-yl]-6-heptenoic acid, methyl ester Following the procedure outlined in Example 1 part G, the title B compound is converted to the title C compound.

D. [1R-(1α,2β(6Z),3β(1E),4α)]-7-[3-(1-Octenyl)-7-oxabicyclo[2.2.1]hept-2-yl]-6-heptenoic acid, methyl ester Following the procedure in Example 2 part A, except substituting the above title C compound for the Example 1 compound, the title D compound in admixture with the title E compound set out below is obtained.

E. [1R-[1α,2β(6Z),3β(1Z),4α)]-7-[3-(1-Octenyl)-7-oxabicyclo[2.2.1]hept-2-yl]-6-heptenoic acid, methyl ester The title E compound is isolated from the title D compound as described in Example 2 part B.

F. [1R-(1α,2β(6Z),3β(1E),4α)]-7-[3-(1-(Octenyl)-7-oxabicyclo[2.2.1]hept-2-yl]-6-heptenoic acid Following the procedure outlined in Example 3 except substituting the above title D compound for the Example 2 part A compound, the above title F compound is obtained.

G. [1R-(1α,2β(6Z)-3β(1Z),4α)]-7-[3-(1-Octenyl)-7-oxabicyclo[2.2.1]hept-2-yl]-6-heptenoic acid Following the procedure outlined in Example 3 except substituting the above title E compound for the Example 2 part A compound, the above title G compound is obtained.

EXAMPLE 8

[1R-(1α,2β(5Z),3β(2Z),4α)]-7-[3-(2-Octenyl)-7-oxabicyclo[2.2.1]hept-2-yl)-5-heptenoic acid A. [1R-(1α,2β(5Z),3β,4α)]-7-[3-(2-Methoxyethenyl)-7-oxabicyclo[2.2.1]-hept-2-yl]-5-heptenoic acid, methyl ester Following the procedure outlined in Example 1 part D, except substituting the Example 1 part G compound for the Example 1 part C compound, the above title A compound is obtained.

B. [1R-(1α,2β(5Z),3β,4α)]-7-[3-(Formylmethyl)-7-oxabicyclo[2.2.1]hept-2-yl]-5-heptenoic acid, methyl ester Following the procedure outlined in Example 4 part A, except substituting the above title A compound for the Example 1 part D compound, the title B compound is obtained.

C. [1R-(1α,2β(5Z),3β(2E),4α)]-7-[3-(2-Octenyl)-7-oxabicyclo[2.2.1]hept-2-yl]-5-heptenoic acid, methyl ester Following the procedure outlined in Example 2 the Wittig reagent prepared from hexyl triphenyl phosphonium bromide is used to convert the title B compound to a mixture of the title C compound and the title D compound mentioned below.

D. [1R-(1α,2β(5Z),3β(2Z),4α)]-7-[3-(2-Octenyl)-7-oxabicyclo[2.2.1]hept-2-yl]-5-heptenoic acid, methyl ester The above title D compound is isolated from the title C compound as described in Example 2 part B.

E. [1R-[1α,2β(5Z),3β(2E),4α)]-7-[3-(2-Octenyl)-7-oxabicyclo[2.2.1]hept-2-yl)-5-heptenoic acid Following the procedure outlined in Example 3 except substituting the above title C compound for the Example 2 part A compound, the above title E compound is obtained.

F. [1R-(1α,2β(5Z),3β(2Z),4α)]-7-[3-(2-Octenyl)-7-oxabicyclo[2.2.1]hept-2-yl)-5-heptenoic acid Following the procedure outlined in Example 3 except substituting the above title D compound for the Example 2 part A compound, the above title F compound is obtained.

EXAMPLE 9

[1R-(1α,2β(5Z),3β(3Z),4α)]-7-[3-(3-Octenyl)-7-oxabicyclo[2.2.1]hept-2-yl]-5-heptenoic acid A. [1R-(1α,2β(5Z),3β,4α)]-7-[3-(3-Methoxy-2-propenyl)-7-oxabicyclo[2.2.1]hept-2-yl]-5-heptenoic acid, methyl ester Following the procedure outlined in Example 1 part D, except substituting the Example 8 part B compound for the Example 1 part C compound, the above title A compound is obtained.

B. [1R-(1α,2β(5Z),3β,4α)]-7-[3-(2-Formylethyl)-7-oxabicyclo[2.2.1]hept-2-yl]-5-heptenoic acid, methyl ester Following the procedure outlined in Example 4 part A except substituting the above title A compound for the Example 1 part D compound, the title B compound is obtained.

C. [1R-(1α,2β(5Z),3β(3E),4α)]-7-[3-(3-Octenyl)-7-oxabicyclo[2.2.1]hept-2-yl]-5-heptenoic acid, methyl ester The procedure used to prepare the compound of Example 2 is used with the Wittig reagent prepared from pentyl triphenyl phosphonium bromide to convert the above title B compound to the above title C compound in admixture with the title D compound mentioned below.

D. [1R-(1α,2β(5Z),3β(3Z),4α)]-7-[3-(3-Octenyl)-7-oxabicyclo[2.2.1]hept-2-yl]-5-heptenoic acid, methyl ester The above title D compound is isolated from the title C compound as described in Example 2 part B.

E. [1R-(1α,2β(5Z),3β(3E),4α)]-7-[3-(3-Octenyl)-7-oxabicyclo[2.2.1]hept-2-yl]-5-heptenoic acid Following the procedure outlined in Example 3 except substituting the above title C compound for the Example 2 part A compound, the above title E compound is obtained.

F. [1R-(1α,2β(5Z),3β(3Z),4α)]-7-[3-(3-Octenyl)-7-oxabicyclo[2.2.1]hept-2-yl]-5-heptenoic acid Following the procedure outlined in Example 3 except substituting the above title D compound for the Example 2 part A compound, the above title F compound is obtained.

EXAMPLE 10

[1R-(1α,2β(5Z),3β(4Z),4α)]-7-[3-(4-Octenyl)-7-oxabicyclo[2.2.1]hept-2-yl]-5-heptenoic acid A. [1R-(1α,2β(5Z),3β,4α)]-7-[3-(4-Methoxy-3-butenyl)-7-oxabicyclo[2.2.1]hept-2-yl[-5-heptenoic acid, methyl ester Following the procedure outlined in Example 1 part D, except substituting the Example 9 part B compound for the Example 1 part C compound, the above title A compound is obtained.

B. [1R-(1α,2β(5Z),3β,4α)]-7-[3-(3-Formylpropyl)-7-oxabicyclo[2.2.1]hept-2-yl]-5-heptenoic acid, methyl ester Following the procedure outlined in Example 4 part A except substituting the above title A compound for the Example 1 part D compound, the title B compound is obtained.

C. [1R-(1α,2β(5Z),3β(4E),4α)]-7-(3-(4-Octenyl)-7-oxabicyclo[2.2.1]hept-2-yl]-5-heptenoic acid, methyl ester The procedure used to prepare the compound of Example 2 is used with the Wittig reagent prepared from butyl triphenylphosphonium bromide to convert the above title B compound to the above title C compound in admixture with the title D compound mentioned above.

D. [1R-(1α,2β(5Z),3β(4Z),4α)]-7-(3-(4-Octenyl)-7-oxabicyclo[2.2.1]hept-2-yl]-5-heptenoic acid, methyl ester The above title D compound is isolated from the title C compound as described in Example 2 part B.

E. [1R-(1α,2β(5Z),3β(4E),4α)]-7-[3-(4-Octenyl)-7-oxabicyclo[2.2.1]-hept-2-yl]-5-heptenoic acid Following the procedure outlined in Example 3 except substituting the above title C compound for the Example 2 part A compound, the above title E compound is obtained.

F. [1R-(1α,2β(5Z),3β(4Z),4α)]-7-[3-(4-Octenyl)-7-oxabicyclo[2.2.1]-hept-2-yl]-5-heptenoic acid Following the procedure outlined in Example 3 except substituting the above title D compound for the Example 2 part A compound, the above title F compound is obtained.

EXAMPLE 11

[1R-(1α,2β(5Z),3β(5Z),4α)]-7-[3-(5-Octenyl)-7-oxabicyclo[2.2.1]hept-2-yl]-5-heptenoic acid A. [1R-(1α,2β(5Z),3β,4α)]-7-[3-(5-methoxy-4-pentenyl)-7-oxabicyclo[2.2.1]hept-2-yl]-5-heptenoic acid, methyl ester Following the procedure outlined in Example 1 part D, except substituting the Example 10 part B compound for the Example 1 part C compound, the above title A compound is obtained.

B. [1R-(1α,2β(5Z),3β,4α)]-7-[3-(4-Formylbutyl)-7-oxabicyclo[2.2.1]hept-2-yl]-5-heptenoic acid, methyl ester Following the procedure outline in Example 4 part A except substituting the above title A compound for the Example 1 part D compound, the title B compound is obtained.

C. [1R-(1α,2β(5Z),3β(5E),4α)]-7-[3-(5-Octenyl)-7-oxabicyclo[2.2.1]hept-2-yl]-5-heptenoic acid, methyl ester The procedure used to prepare the compound of Example 2 is used with the Wittig reagent prepared from propyl triphenylphosphonium bromide to convert the above title B compound to the above title C compound in admixture with the title D compound mentioned below.

D. [1R-(1α,2β(5Z),3β(5Z),4α)]-7-[3-(5-Octenyl)-7-oxabicyclo[2.2.1]hept-2-yl]-5-heptenoic acid, methyl ester The above title D compound is isolated from the title C compound as described in Example 2 part B.

E. [1R-(1α,2β(5Z),3β(5E),4α)]-7-[3-(5-Octenyl)-7-oxabicyclo[2.2.1]hept-2-yl]-5-heptenoic acid Following the procedure outlined in Example 3 except substituting the above title C compound for the Example 2 part A compound, the above title E compound is obtained.

F. [1R-(1α,2β(5Z),3β(5Z),4α)]-7-[3-(5-Octenyl)-7-oxabicyclo[2.2.1]hept-2-yl]-5-heptenoic acid Following the procedure outlined in Example 3 except substituting the above title D compound for the Example 2 part A compound, the above title F compound is obtained.

EXAMPLE 12

[1R-(1α,2β(5Z),3β(6Z),4α)]-7-[3-(6-Octenyl)-7-oxabicyclo[2.2.1]hept-2-yl]-5-heptenoic acid A. [1R-(1α,2β(5Z),3β,4α)]-7-[3-(6-Methoxy-5-hexenyl)-7-oxabicyclo[2.2.1]hept-2-yl]-5-heptenoic acid, methyl ester Following the procedure outlined in Example 1 part D, except substituting the Example 11 part B compound for the Example 1 part C compound, the above title A compound is obtained.

B. [1R-(1α,2β(5Z),3β,4α)]-7-[3-(5-Formylpentyl)-7-oxabicyclo[2.2.1]-hept-2-yl]-5-heptenoic acid, methyl ester Following the procedure outlined in Example 4 part A except substituting the above title A compound for the Example 1 part D compound, the title B compound is obtained.

C. [1R-(1α,2β(5Z),3β(6E),4α)]-7-[3-(6-Octenyl)-7-oxabicyclo[2.2.1]hept-2-yl]-5-heptenoic acid, methyl ester The procedure used to prepare the compound of Example 2 is used with the Wittig reagent prepared from ethyl triphenylphosphonium bromide to convert the above title B compound to the above title C compound in admixture with the title D compound mentioned below.

D. [1R-(1α,2β(5Z),3β(6Z),4α)]-7-[3-(6-Octenyl)-7-oxabicyclo[2.2.1]hept-2-yl]-5-heptenoic acid, methyl ester The above title D compound is isolated from the title C compound as described in Example 2 part B.

E. [1R-(1α,2β(5Z),3β(6E),4α)]-7-[3-(6-Octenyl)-7-oxabicyclo[2.2.1]hept-2-yl]-5-heptenoic acid Following the procedure outlined in Example 3 except substituting the above title C compound for the Example 2 part A compound, the above title E compound is obtained.

F. [1R-(1α,2β(5Z),3β(6Z),4α)]-7-[3-(6-Octenyl)-7-oxabicyclo[2.2.1]hept-2-yl]-5-heptenoic acid Following the procedure outlined in Example 3 except substituting the above title D compound for the Example 2 part A compound, the above title F compound is obtained.

EXAMPLE 13

[1R-(1α,2β(5Z),3β(7Z),4α)]-7-[3-(7-Octenyl)-7-oxabicyclo[2.2.1]hept-2-yl]-5-heptenoic acid A. [1R-(1α,2β(5Z),3β,4α)]-7-[3-(7-Methoxy-6-heptenyl)-7-oxabicyclo[2.2.1]hept-2-yl]-5-heptenoic acid, methyl ester Following the procedure outlined in Example 1 part D, except substituting the Example 12 part B compound for the Example 1 part C compound, the above title A compound is obtained.

B. [1R-(1α,2β(5Z),3β,4α)]-7-[3-(6-Formylhexyl)-7-oxabicyclo[2.2.1]hept-2-yl]-5-heptenoic acid, methyl ester Following the procedure outlined in Example 4 part A except substituting the above title A compound for the Example 1 part D compound, the title B compound is obtained.

C. [1R-(1α,2β(5Z),3β(7E),4α)]-7-[3-(7-Octenyl)-7-oxabicyclo[2.2.1]hept-2-yl]-5-heptenoic acid, methyl ester The procedure used to prepare the compound of Example 2 is used with the Wittig reagent prepared from methyl triphenylphosphonium bromide to convert the above title B compound to the above title C compound in admixture with the title D compound mentioned below.

D. [1R-(1α,2β(5Z),3β(7Z),4α)]-7-[3-(7-Octenyl)-7-oxabicyclo[2.2.1]hept-2-yl]-5-heptenoic acid, methyl ester The above title D compound is isolated from the title C compound as described in Example 2 part B.

E. [1R-(1α,2β(5Z),3β(7E),4α)]-7-[3-(7-Octenyl)-7-oxabicyclo[2.2.1]hept-2-yl]-5-heptenoic acid Following the procedure outlined in Example 3 except substituting the above title C compound for the Example 2 part A compound, the above title E compound is obtained.

F. [1R-(1α,2β(5Z),3β(7Z),4α)]-7-[3-(7-Octenyl)-7-oxabicyclo[2.2.1]hept-2-yl]-5-heptenoic acid Following the procedure outlined in Example 3 except substituting the above title D compound for the Example 2 part A compound, the above title F compound is obtained.

What is claimed is:

1. A compound of the formula

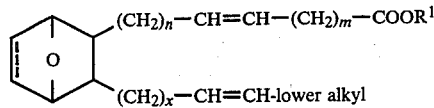

wherein
R$^1$ is hydrogen or lower alkyl; n is 0 to 4, m is 0 to 4 and x is 0 to 8.

2. The compound of claim 1 wherein n is 1 and m is 3.

3. The compound of claim 2 wherein x is 0 and the lower alkyl attached to the olefinic carbon atom contains 4 to 6 carbons.

4. The compound of claim 1 wherein R$^1$ is methyl.

5. The compound of claim 1 having the name [1R-(1α,2β(5Z),3β(1E),4α)]-7-[3-(1-octenyl)-7-oxabicyclo[2.2.1]hept-2-yl]-5-heptenoic acid.

6. The compound of claim 1 having the name [1R-(1α,2β(5Z),3β(1E),4α]-7-[3-(1-octenyl)-7-oxabicyclo[2.2.1]hept-2-yl]-5-heptenoic acid.

7. A method of inhibiting arachidonic acid-induced platelet aggregation and bronchoconstriction, which comprises administering to the circulatory system of a mammalian host an effective amount of a compound as defined in claim 1 or a pharmaceutically acceptable salt thereof.

8. The method as defined in claim 7 wherein said compound is administered in an amount within the range of from about 1 to about 100 mg/kg.

9. A composition for inhibiting arachidonic acid-induced platelet aggregation and bronchoconstriction, comprising an effective amount of a compound as defined in claim 1 or a pharmaceutically acceptable salt thereof, and a pharmaceutically acceptable carrier therefor.

10. A method of inhibiting platelet aggregation which comprises administering to a mammalian host an effective amount of a compound as defined in claim 1 or a pharmaceutically acceptable salt thereof.

11. A method of inhibiting bronchoconstriction associated with asthma, which comprises administering to a mammalian host an effective amount of a compound as defined in claim 1 or a pharmaceutically acceptable salt thereof.

UNITED STATES PATENT AND TRADEMARK OFFICE
CERTIFICATE OF CORRECTION

PATENT NO. : 4,228,180
DATED : October 14, 1980
INVENTOR(S) : Peter W. Sprague

It is certified that error appears in the above-identified patent and that said Letters Patent are hereby corrected as shown below:

Column 3, Structure XII should read -- 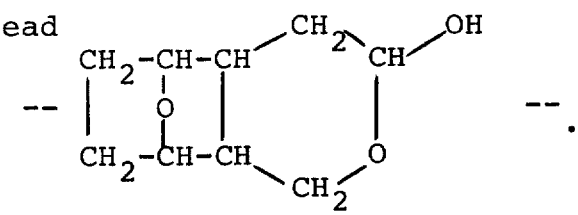 --.

Column 6, line 31, "XIVb" should read --XIVd--.
Column 10, line 50, "dialy" should read --daily--.
Column 10, line 58, "so" should read --as--.

Signed and Sealed this

Twenty-seventh Day of January 1981

[SEAL]

Attest:

RENE D. TEGTMEYER

Attesting Officer

Acting Commissioner of Patents and Trademarks